United States Patent [19]

Hermecz et al.

[11] 4,252,807
[45] * Feb. 24, 1981

[54] FUSED PYRIMIDINE DERIVATIVES AND ANTIATHEROSCLEROTIC METHODS OF TREATMENT WITH THEM

[75] Inventors: Istvan Hermecz; Zoltan Meszaros; Sandor Virag; Lelle Vasvari; Agnes Horvath; Jozsef Knoll; Gyula Sebestyen; Agoston David, all of Budapest, Hungary

[73] Assignee: Chincin Gyogyszer es Vegyeszeti Termekek Gyara Rt., Budapest, Hungary

[*] Notice: The portion of the term of this patent subsequent to Oct. 31, 1995, has been disclaimed.

[21] Appl. No.: 931,908

[22] Filed: Aug. 8, 1978

Related U.S. Application Data

[62] Division of Ser. No. 765,595, Feb. 4, 1977, Pat. No. 4,123,533.

[30] Foreign Application Priority Data

Feb. 12, 1976 [HU] Hungary ................................ 1642

[51] Int. Cl.³ .................. A61K 31/505; C07D 471/04
[52] U.S. Cl. .................................. 424/251; 542/405; 542/442; 542/443; 542/444; 544/282
[58] Field of Search ............... 544/282, 252; 424/251; 542/448, 452, 449, 468, 469, 475, 405, 442, 443, 444

[56] References Cited

U.S. PATENT DOCUMENTS

| 3,376,304 | 4/1968 | Mohrbacher et al. | 546/350 |
|---|---|---|---|
| 3,567,719 | 3/1971 | Eldredge et al. | 544/282 |
| 3,635,956 | 1/1972 | Krapcho | 542/252 X |
| 3,696,197 | 10/1972 | Meszaros et al. | 424/251 |
| 3,897,420 | 7/1975 | Krapcho et al. | 542/452 |
| 3,898,224 | 8/1975 | Yale et al. | 424/251 X |
| 3,929,787 | 12/1975 | Yale | 424/251 X |
| 3,935,197 | 1/1976 | Yale | 424/251 X |

OTHER PUBLICATIONS

Gupta et al., Indian Journal of Chemistry, vol. 9, pp. 201–206, 3/71.

Primary Examiner—Donald G. Daus
Assistant Examiner—Diana G. Rivers
Attorney, Agent, or Firm—Karl F. Ross

[57] ABSTRACT

An optically active or racemic fused pyrimidine derivative of the formula I

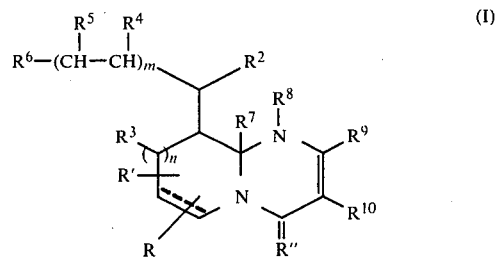

has pharmaceutical activity in decreasing serum lipids, cholesterol deposits and, in general, against atherosclerosis.

18 Claims, No Drawings

FUSED PYRIMIDINE DERIVATIVES AND ANTIATHEROSCLEROTIC METHODS OF TREATMENT WITH THEM

CROSS REFERENCE TO RELATED APPLICATION

The application is a division of Ser. No. 765,595 filed Feb. 4, 1977, now U.S. Pat. No. 4,123,533.

DESCRIPTION OF THE INVENTION

The present invention relates to new optionally racemic or optically active fused pyrimidine derivatives of the formula

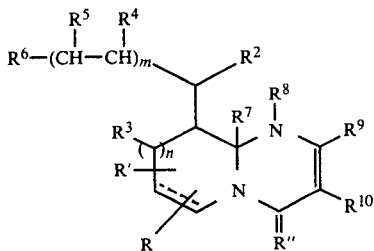

or the salts thereof, wherein
n=0, 1, 2 or 3; m=0, 1 or 2

R is hydrogen, optionally (substituted i.e. substituted or unsubstituted) amino, optionally substituted alkyl, optionally substituted hydroxyl, optionally substituted aryl, optionally substituted aralkyl, carboxyl or a group derived from the carboxyl group;

$R^1$ is hydrogen, optionally substituted alkyl group or R and $R^1$ together form a —(CH=CH)$_2$-chain, wherein the dotted line represents an optional valency bond;

$R^2$ stands for a hydrogen atom, a hydroxyl, alkoxy, mercapto, O-acyl or an optionally substituted amino group;

$R^3$ is hydrogen, or optionally together with $R^2$ represents a valency bond;

$R^4$ and $R^5$ independently represent a hydrogen atom or together form a valency bond;

$R^6$ is hydrogen, optionally substituted aryl, optionally substituted heterocyclic, or carboxyl, a group derived from the carboxyl group or a trihalomethyl group;

$R^7$ and $R^8$ independently represent a hydrogen atom or together form a valency bond;

$R^9$ is hydrogen, optionally substituted hydroxyl, optionally substituted amino, alkylthio, optionally substituted alkyl, optionally substituted aryl, optionally substituted aralkyl, carboxyl, a group derived from the carboxyl group, a heterocyclic group containing nitrogen being attached to the pyrimidine ring through a nitrogen atom, $R^{10}$ is hydrogen, optionally substituted alkyl, optionally substituted aryl, optionally substituted aralkyl, optionally substituted amino, carboxyl group, cyano group, a group derived from the carboxyl group, an optionally substituted acyl group; and R and R together can form a —(CH$_2$)$_p$-chain, wherein p represents a number from 3 through 10, $R^{11}$ stands for an oxygen or sulfur atom or an $R^{12}$—N= -group, wherein $R^{12}$ represents a hydrogen atom or an acyl group.

The new optionally racemic or optically active fused pyrimidine derivatives provided by the invention and the salts thereof may be prepared according to the invention (a) by reacting an optionally racemic fused pyrimidine derivative of the formula

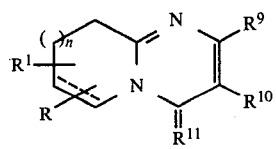

wherein R, $R^1$, $R^9$, $R^{10}$, $R^{11}$, n and the dotted line have the same meaning as defined above, with an aldehyde of the formula

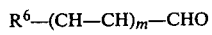

$$R^6\text{—}(CH\text{—}CH)_m\text{—}CHO \quad (III)$$

wherein R and m have the same meaning as defined above, and optionally transforming the thus obtained fused pyrimidine derivative of the formula I, in which $R^4$ and $R^5$ as well as $R^7$ and $R^8$, respectively together form a chemical bond and $R^2$ stands for a hydroxyl group, $R^3$ stands for a hydrogen atom, by dehydration into a fused pyrimidine derivative of the formula I, in which $R^2$ and $R^3$ together form a valency bond; or (b) by reacting an optionally optically active fused pyrimidine derivative of the formula II with an aldehyde derivative of the formula

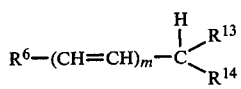

wherein
$R^{13}$ and $R^{14}$ may be identical or different, thus may stand for a hydroxy, alkoxy, an optionally substituted amino, O-acyl or —SO$_3$Na group, or
$R^{13}$ and $R^{14}$ together may form a =S or =N-$R^{15}$ group, wherein R represents a hydrogen atom, an alkyl or optionally substituted aryl group, and optionally transforming the thus obtained optionally optically active fused pyrimidine derivative of the formula I, in which $R^4$ and $R^5$ as well as $R^7$ and $R^8$, respectively together form a valency bond, and $R^2$ represents a hydroxyl, alkoxy, optionally substituted amino, —O-acyl, mercapto group, $R^3$ stands for a hydrogen atom, by splitting off a compound of the formula $R^2H$, wherein $R^2$ stands for a hydroxyl, alkoxy, optionally substituted amino, —O-acyl, mercapto group, into an optionally optically active fused pyrimidine derivative of the formula I, in which $R^2$ and $R^3$ together form a valency bond, and if desired, by transforming groups $R^6$, $R^9$, $R^{10}$ and $R^{11}$ into other $R^6$, $R^9$, $R^{10}$ and $R^{11}$ groups, by per se known methods and/or by saturating the valency bonds formed by the attachment of $R^2$ and $R^3$, $R^4$ and $R^5$ as well as $R^7$ and $R^8$, respectively by hydrogenation in an optional order, gradually or simultaneously and optionally by transforming the thus obtained optionally optically active fused pyrimidine derivative of the formula I into its acid addition salts with a pharmaceutically acceptable inorganic or organic acid, or into its salts with a pharmaceutically acceptable inorganic or organic base and/or, if desired, setting it free from its salt or transforming it into an other salt of same, and if desired preparing optically active compounds of the formula I by resolution of the racemic compound of the formula I or by using optically active starting materials in step (a) or (b).

Process variants (a) and (b) can be performed in a suitable solvent or without any solvent, preferably at a temperature from −20° C. to 250° C.

As solvents there may be used protic, apolar or dipolar aprotic solvents or the mixtures thereof.

Suitable protic solvents are the following: alkanols having 1 to 6 carbon atoms, e.g. methanol, ethanol, iso-propanol, glycerin etc.;
aliphatic carboxylic acids, e.g. formic acid, acetic acid; formamide etc.

As apolar solvent there may be used hydrocarbons, e.g. benzene, toluene, xylene etc.; chlorinated hydrocarbons, e.g. chloroform, carbontetrachloride, chlorobenzene etc.; ethers, e.g. diethylether, tetrahydrofurane, dioxane etc.

As dipolar solvents there may be used dimethyl formamide, dimethyl acetamine, dimethyl sulfoxide, ketones, e.g. acetone, ethyl methyl ketone etc.; nitro benzene; aceto nitrile; hexamethyl phosphorous triamide etc.

Suitably chosen mixtures of the above-listed solvents can be also applied.

When carrying out process variants (a) and (b) if desired, also basic or acidic catalysts can be used. Also the suitably chosen solvent itself may act as a catalyst. Thus solvents such as acetic acid or formic acid may perform a double role, since they may act as acidic catalysts and as solvents at the same time.

Additionally acidic catalysts may be applied such as inorganic or organic acids, e.g. hydrochloric acid, sulphuric acid, phosphoric acid, acetic acid etc.

As basic catalysts there may be used piperidine, diethyl amine and bifunctional catalysts such as piperidine acetate and pyridine, which are able to function as acidic and basic catalysts as well.

If desired, the reaction of process variant (a) and (b) respectively can be conducted also in such a way that instead of the addition-products, i.e. the compounds of the formula I, in which $R^2$ stands for a hydroxyl, mercapto, alkoxy, optionally substituted amino group and $R^3$ stands for a hydrogen atom, the condensation-products, i.e. pyrimidine derivatives of the formula I in which $R^2$ and $R^3$ together form a valency bond, are obtained.

If required $R^6$ can be transformed into a different $R^6$ substituent by per se known methods. Thus, a carboxyl $R^6$ may be transformed into the corresponding ester group with a suitable alcohol. The esterification may be carried out by the methods known in the art for this purpose. For example the reaction preferably can be accomplished by bubbling dry hydrogen chloride gas through the alcohol solution, when esterification takes place, or by heating the mixture of carboxylic acid and alcohol in the presence of concentrated sulphuric acid, and eliminating the formed water by axeotropic distillation, with benzene or chloroform. A carboxyl $R^6$ can be transformed, if desired, also to an acid amide through a suitable active ester, prepared by means of triethylamine or chloroformic acid, with ammonia or to an N-substituted acid amide group with other amines.

If $R^6$ stands for an ester group, it can be converted into another ester with a different kind of alcohol, preferably in the presence of hydrogen chloride, or can be transformed into an acid amide group with ammonia, for example in an alcohol solution, into a carbohydrazide group with hydrazine hydrate and into an N-substituted acid amine group with amines.

An optionally substituted acid amide group can be prepared also by transforming the carboxyl $R^6$ into an acid halide group by means of thionyl chloride, phosphorous oxychloride, phosphorous pentachloride etc. and reacting the obtained compound with an optionally substituted amine or with ammonia.

If $R^6$ stands for an acid amide group it can be transformed into a nitrile group by water. The water may be extracted for example using phosphorous oxychloride, phosphorous pentoxide, thionyl chloride etc.

If $R^6$ represents a nitrile group, it can be transformed into an amidine group with ammonia, into an acid amide group with water and into a thioacid amide group with hydrogen sulphide.

If desired, an ester, acid amide or nitrile $R^6$ may be transformed into a carboxy group by acidic or alkaline hydrolysis. The obtained carboxyl group, if desired, can be removed when a hydrogen atom remains. The decarboxylating reaction may be carried out under heating, preferably in quinoline, polyphosphoric acid etc.

The substituents represented by $R^9$ can be transformed into different substituents by methods known in the art. For example the ester, acid amide and nitrile groups may be subjected to the above-described transformations.

If desired, also the substituents represented by $R^{10}$ can be transformed into different substituents. For example if $R^{10}$ stands for carboxyl, ester, acid amide or nitrile groups, it can be subjected to the transformations described in connection with $R^6$.

If desired, the substituents represented by $R^{11}$ can be transformed into a different substituent by methods known in the art. For example if $R^{11}$ stands for an oxygen atom, it can be reacted with phosphorous pentasulphide in pyridine, when a sulphur atom is obtained; or if $R^{11}$ represents an =NH group, it may be acylated with an acid halogenide or acid anhydride preparing an =N-acyl group; or an =N-$R^{12}$ group represented by $R^{11}$ can be transformed into an oxygen atom with alkaline hydrolysis.

The obtained compounds of the formula I, if desired, can be transformed into their salts with pharmaceutically acceptable acids. As acids there may be used for example hydrochloric acid, hydrogen bromide, sulphuric acid, phosphorous acid, lactic acid, tartaric acid, maleic acid, nicotinic acid etc.

In the case where at least one of the substituents represented by $R^6$, $R^9$ or $R^{10}$ is a carboxyl group or a group derived from a carboxyl acid also the salts of the compounds of the formula I prepared with bases can be prepared.

There can be advantageously prepared the salts of the compounds of the formula I formed with alkali metals, preferably with sodium, potassium; with alkali earth metals, preferably with calcium, magnesium, with aluminium, vanadium, ethylene diamine, 2-aminoethanol, 2-dimethylamino-ethanol, diidopropyl amine, etc.

The present invention includes also the geometric and optical isomers of the fused pyrimidine derivatives of the formula I.

The optically active compounds of the formula I can be prepared by subjecting a racemic compound of the formula I to resolution by methods known per se or by using an optically active starting material in reactions (a) or (b).

The term "optionally substituted hydroxyl group" as used herein and hereinbefore indicates a hydroxyl group, an alkoxy group having one to 6 carbon atoms, preferably a methoxy, ethoxy group, an aralkoxy group having 7 to 12 carbon atoms, preferably a benzyloxy group, an aryloxy group having 6 to 10 carbon atoms, preferably a phenoxy group.

The term "optionally substituted amino group" represents an amino group optionally bearing one or two identical or different substituents, such as an alkanoylamino group having one to 6 carbon atoms, preferably an acetylamino or propionylamino group, an aroylamino group having 6 to 10 carbon atoms, preferably a benzoylamino group, an alkylamino group having one to 6 carbon atoms, preferably a methylamino or ethylamino group, a dialkylamino group having 1 to 6 carbon atoms, in both alkyls, preferably a dimethylamino or diethylamino group, an aralkylamino group having 7 to 12 carbon atoms, preferably a benzylamino group, an arylamino group having 6 to 10 carbon atoms, preferably a phenylamino group, a piperidyl, pyrrolidinyl or a piperazinyl group.

The term "optionally substituted alkyl group" as used herein and hereinbelow means an alkyl group having one to 6 carbon atoms, preferably a methyl, ethyl, n-propyl group etc., which may bear one or more hydroxyl groups, preferably a 1-hydroxy-ethyl group, carboxyl group or a group derived from the carboxyl acid e.g. alkoxycarbonyl, carboxamido, nitrile group etc.

The term "optionally substituted aryl group" as used herein represents a phenyl group optionally bearing one or more substituents selected from the following groups: alkyl having one to 6 carbon atoms, dialkylamino, nitro, alkoxy, methylendioxy, halogen, alkylthio having one to 6 carbon atoms, carboxyl group or a group derived from a carboxylic acid.

The term "optionally substituted aralkyl group" means an aralkyl group having 7 to 12 carbon atoms optionally substituted with one or more alkyl, alkoxy, halogen, amino, or nitro group.

The term "group derived from the carboxyl group" as used herein indicated an alkoxycarbonyl having one to 6 carbon atoms in the alkyl group, or an alkoxycarbonyl having 7 to 12 carbon atoms, optionally substituted aryloxycarbonyl having 6 to 10 carbon atoms, alkoxythiocarbonyl having one to 6 carbon atoms in the alkyl group, optionally substituted acid amide, acid hydrazide, optionally substituted amidine or nitrile.

The term "optionally substituted acid amide" as used herein means an acid amide, N-alkyl, N,N-dialkyl-, N-phenylalkyl-, N-acyl-acid amide group.

The term "optionally substituted heterocyclic group" as used herein and herein below represents five-, six- or seven-membered monocyclic; nine-, ten- or eleven-membered bicyclic, or 14-membered tricyclic heterocyclic rings containing one or more oxygen, sulphur or nitrogen atom(s) optionally substituted with one or more of the following groups: alkyl having 1 to 6 carbon atoms, nitro, alkoxy, halogen, methylendioxy, dialkylamino.

The heterocyclic ring is preferably a furane, pyrrol, pyridyl, quinolyl ring etc.

The optionally optically active compounds of the formula II used as starting materials may be prepared according to the procedures described in our Hungarian Pat. Nos. 156,119; 158,085; 162,384; 162,373; and 166,577 as well as in our Dutch Pat. No. 7,212,286 or with other similar methods.

The starting materials having the formulas III and IV are commercially available products.

As aldehydes of the formula III there may be used preferably benzaldehyde, isovanilline, vanilline, trimethoxy benzaldehyde, o-chloro-benzaldehyde, p-chloro-benzaldehyde, glyoxylic acid monohydrate, glyoxylic acid, methylendioxy benzaldehyde, 5-nitro-2-furane-aldehyde, 2-thiophene-aldehyde, pyridine-3-aldehyde, pyridine-2-aldehyde, pyridine-4-aldehyde, cinnamic aldehyde, o-cinnamic-aldehyde, fluoro-benzaldehyde, trifluoromethyl aldehyde, methyl benzaldehyde, furfurol, 2-pyrrol-aldehyde, 1-methyl-2-pyrrol-aldehyde, diethoxy benzaldehyde, bromo-benzaldehyde, hydroxy-benzaldehyde, veratrum aldehyde, anis aldehyde, salicyl aldehyde, dimethylamino benzaldehyde, nitro benzaldehyde, alkoxy-carbonyl benzaldehyde, phthalic aldehyde, terephthalic aldehyde, formaldehyde, chloral, bromal etc.

As compounds of the formula IV there may be used for example a hemi-acetal, acetal, acylal, geminal diamine, geminal amino alcohol, Schiff-base, geminal glycol, aldehyde sodium bisulphite, aldehyde cyanohydrine.

The compounds of the formula I possess valuable pharmaceutical properties. They are especially effective against atherosclerosis, influencing not only the serum lipids, but decreasing the quantity of the lipids, deposited in vein walls, especially cholesterin.

The compounds of formula I have favorable toxical properties. The $LD_{50}$-value obtained on rabbits (p.o.) generally is over 2000 mg/kg.

The pharmaceutical activity of the compounds according to the invention was proved using various experimental set-ups. In the following Table 1 there are summarized the results obtained on cholesterin-fed rabbit atherosclerosis model (Beitr. path. Anat. 56, 379–403 (9113).

It can be seen from the data of Table 1 that compounds "C" and "D" result in a significant decrease in the serum lipid, aorta lipid and cholesterin lipid level as well.

TABLE 1

| Substance | Dose mg/kg | Serum | | | Aorta | |
|---|---|---|---|---|---|---|
| | | total lipid | total cholesterin | tri-glyceride | total lipid | total cholesterin |
| Control-1 | — | 658 | 326 | 75 | 1928 | 331 |
| Control-2 | — | 2374 | 1504 | 103 | 2575 | 921 |
| Chlofibrate | 250 | 1938 | 1137 | 115 | 2227 | 787 |
| A | 50 | 2309 | 1419 | 121 | 2496 | 958 |
| B | 50 | 2547 | 1531 | 190 | 2461 | 365 |
| C | 50 | 1903 | 1176 | 119 | 1878 | 353 |
| D | 50 | 1638 | 972 | 97 | 1355 | 186 |

To make our table synoptical we have not listed in the mathematical-statistical data.

A = 6-methyl-9-(N-methyl-2-pyrrolyl)-methylene-4-oxo-6,7,8,9-tetrahydro-4H-pyrido(1,2a) pyrimidine-3-carboxylic acid ethylester B = 6-methyl-9-chloro-phenyl)-methylene-4-oxo-6,7,8,9-tetrahydro-4H-pyrido(1,2a)pyrimidine-3-carboxylic acid ethylester C = 6-methyl-9-(ethoxycarbonyl-methylene)-4-oxo-6,7,8,9-tetrahydro-4H-pyrido(1,2a)-purimidine-3-carboxylic acid ethylester D=6-methyl-3-ethoxycarbonyl-4-oxo-6,7,8,9-tetrahydro-4H-pyrido(1,2a)pyrimidine-9-yl-acetic acid.

In the group "Control-1" rabbits were fed with a normal feed while the rabbits in the "Control-2" group there also received 2 g of cholesterin.

Evaluating the experiments we found that the tested compound in contrast to the Chlorofibrate did not increase the weight of the liver in test animals.

The results obtained on normolyphaemic rats are listed in the following Table 2.

TABLE 2

| Substance | Dose mg/kg p.o. | Serum triglyceride | cholesterine |
|---|---|---|---|
| Control | — | 185.1 | 103 |
| Chlofibrate | 250 | 144.1 | 63.9 |
| E | 50 | 127.9 | 86.5 |
| F | 50 | 155.5 | 88.0 |
| G | 50 | 127.5 | 88.0 |
| H | 50 | 107.9 | 90.2 |

E=9-(ethoxycarbonyl-methylene)-4-oxo-6,7,8,9-tetrahydro-4H-pyrido(1,2a)pyrimidine-3-carboxylic acid ethylester F=9-(carboxyl-methyl)-4-oxo-1,6,7,8,9,9a-hexahydro-4H-pyrido(1,2a)pyrimidine-3-carboxylic acid ethylester G=9-(carboxyl-methyl)-4-oxo-6,7,8,9-tetrahydro-4H-pyrido-(1,2a)pyrimidine-3-carboxylic acid ethylester H=9-(methoxycarbonyl-methylene)-6-methyl-4-oxo-6,7,8,9-tetrahydro-4H-pyrido(1,2a)pyrimidine-3-carboxylic acid methylester For the sake of simplicity the mathematical-statistical data have been omitted also in Table 2.

Other representatives of the compounds according to the present invention show a significant central neurotic system(CNS) activity. Thus some of the compounds exhibit significant degrees of analgesic, antipyretic, antiinflammatory activity, tranquillizer narcotic potentiating activity, liver-protective, antidepressive, antibacterial or antituberculotic as well as anti-asthmatic activity.

The compounds prepared according to the invention find their application chiefly as pharmaceuticals but may be applied also as starting substances for the preparation of other, pharmaceutically active compounds.

The compounds of the formula I according to the invention may be applied in various application forms prepared by admixing them with inert, non-toxic solid or liquid diluents or carriers. The compositions may be finished as solid formulations, e.g. tablets, capsules, dragees, perl-capsules, or liquid formulations, e.g. solutions, suspension or emulsions.

The dose depends on the field of the application and of the pharmaceutical form used. Thus generally compositions containing 1 mg to 100 mg of active ingredient may be prepared.

As carriers the generally used substances, such as talcum, calcium carbonate, magnesium stearate, water, polyethylene glycolate may be employed.

The composition contain, if desired, also some other conventionally used excipients, such as emulsifiers, decomposing agents etc.

The compositions, if desired, may be finished also in forms showing retarded activity.

Further details of our invention are to be found in the following Examples.

EXAMPLE 1

The mixture of 23.6 g of 3-ethoxycarbonyl-6-methyl-4-oxo-6,7,8,9-tetrahydro-4H-pyrido(1,2a)pyrimidine and 10.6 g of benzaldehyde is stirred at 40° C. whereupon 10 ml of ethanol are added and the reaction mixture is allowed to stand overnight. The precipitated crystals are filtered off. White 3-ethoxy-carbonyl-9-(1'-hydroxy-benzyl)-6-methyl-4-oxo-6,7,8,9-tetrahydro-4H-pyrido(1,2a)pyrimidine is obtained melting after recrystallization from ethanol at 186° to 187° C.

Analysis: Calculated: C 66.65%, H 6.48%, N 8.18%: Found: C 66.72%, H 6.50%, H 8.19%.

EXAMPLE 2

According to the method described in Example 1 but using chloral or chloral hydrate as the aldehyde component 3-ethoxycarbonyl-9-(1-hydroxyl-2,2,2-trichloroethyl)-6-methyl-4-oxo-6,7,8,9-tetrahydro-4H-pyrido(1,2a)pyrimidine is obtained. Melting point after recrystallisation from ethanol: 165° to 166° C. Yield: 61%.

Analysis: Calculated: C 43.83%, H 4.47%, N 7.30%, Cl 27.70%: Found: C 43.70%, H 4.51%, N 7.39%, Cl 27.37%.

EXAMPLE 3

The mixture of 118.0 g of 3-ethoxy-carbonyl-6-methyl-4-oxo-6,7,8,9-tetrahydro-4H-pyrido(1,2a)pyrimidine and 30 g of paraformaldehyde in 1200 ml of ethanol is heated for 2 hours, whereupon 15 g of paraformaldehyde are added to the reaction mixture which is then stirred for an additional one hour. Thereafter there is added an additional 15 g portion of paraformaldehyde and the mixture is boiled for an additional one hour. The reaction mixture is evaporated, the residue is dissolved in 1200 ml of water and shaken out subsequently with benzene and chloroform. After drying the chloroform solution is evaporated, and the residue is recrystallized from ethanol twice to yield 3-ethoxycarbonyl-9,9-di-(hydroxymethyl)-6-methyl-4-oxo-6,7,8,9-tetrahydro-4H-pyrido(1,2a)pyrimidine melting at 119° to 120° C.

Analysis: Calculated: C 56.75%, H 6.80%, N 9.45%: Found: C 56.89%, H 6.80%, N 9.40%.

EXAMPLE 4

34 g of 3-ethoxycarbonyl-9-(1'-hydroxyl-benzyl)-6-methyl-4-oxo-6,7,8,9-tetrahydro-4H-pyrido(1,2a)-pyrimide are boiled in the mixture of 100 ml of ethanol and 10 ml of 15 percent by weight solution of hydrochloric acid in ethanol. Upon cooling the precipitated yellow crystals are filtered off, and recrystallized from ethanol to yield 3-ethoxycarbonyl-9-benzylidene-6-methyl-4-oxo-6,7,8,9-tetrahydro-4H-pyrido(1,2a)pyrimidine. The product does not decrease the melting point of the product prepared according to Example 5, when admixed with that.

EXAMPLE 5

23.6 g of 3-ethoxycarbonyl-6-methyl-4-oxo-6,7,8,9-tetrahydro-4H-pyrido(1,2a)pyrimidine and 10.6 g of benzaldehyde are reacted in the mixture of 10 ml ethanol and 5 ml of 15 percent by weight solution of hydrochloric acid in ethanol. The resulting 3-ethoxycarbonyl-9-(1'-hydroxyl-benzyl)-6-methyl-4-oxo-6,7,8,9-tetrahydro-4H-pyrido(1,2a)pyrimidine is transformed without separation, under further heating and stirring into the yellow 3-ethoxycarbonyl-9-benzylidene-6-methyl-4-oxo-6,7,8,9-tetrahydro-4H-pyrido-(1,2a)pyrimidine.

The melting point of the above compound after recrystallization from ethanol is 140° to 141° C. Yield: 70%.

Analysis: Calculated: C 70.35%, H 6.22%, N 8.64%:
Found: C 70.24%, H 5.99%, N 8.60%

According to the method described in Example 5 using the appropriate starting materials the following compounds listed in Table 3 are prepared.

TABLE 3

[Structure with $R_{16}$-CH=, N, $R_{17}$, $R_{18}$, $R_{19}$ substituents on bicyclic ring system]

| No. | $R_{16}$ | $R_{17}$ | $R_{18}$ | $R_{19}$ | Solvent | Catalyst | M.p. °C. solvent used for crystallization | Yield % | Analysis Calculated Found C% | H% | N% |
|---|---|---|---|---|---|---|---|---|---|---|---|
| 6. | 5-nitro-2-furyl | $CH_3$ | H | $COOC_2H_5$ | pyridine | — | 194–195 | 85 | 56.82 56.75 | 4.77 4.79 | 11.69 11.80 |
| 7. | 2-furyl | $CH_3$ | H | $COOC_2H_5$ | n-propanol | — | 152–154 DMF | 78 | 64.96 64.99 | 5.77 5.68 | 8.91 9.07 |
| 8. | 2-pyrryl | $CH_3$ | H | $COOC_2H_5$ | ethylene glycol | HCl | 246 ethanol | 76 | 65.16 65.03 | 6.11 6.04 | 13.41 13.65 |
| 9. | N-methyl-2-pyrryl | $CH_3$ | H | $COOC_2H_5$ | ethanol | HCl | 165–166 ethanol | 61 | 66.04 65.94 | 6.47 6.43 | 12.84 12.78 |
| 10. | 3,4,5-trimethoxy-phenyl | $CH_3$ | H | $COOC_2H_5$ | ethanol | HCl | 138–141 ethanol | 80 | 63.76 63.49 | 6.32 6.30 | 6.76 6.90 |
| 11. | 3-hydroxy-4-methoxy-phenyl | $CH_3$ | H | $COOC_2H_5$ | ethanol | HCl | 190–192 | 82 | 64.85 65.00 | 5.99 5.90 | 7.56 7.45 |
| 12. | 3,4-methylenedioxy-phenyl | $CH_3$ | H | $COOC_2H_5$ | ethanol | HCl | 140–142 dimethyl-formamide | | 65.21 65.40 | 5.47 5.40 | 7.60 7.86 |
| 13. | 3,4-dimethoxy-phenyl | $CH_3$ | H | $COOC_2H_5$ | ethanol | HCl | 134–135 ethanol | 65 | 65.61 65.86 | 6.29 6.18 | 7.29 7.37 |
| 14. | 4-hydroxy-phenyl | $CH_3$ | H | $COOC_2H_5$ | ethanol | HCl | 240–242 DMF | 88 | 67.05 67.11 | 5.92 5.78 | 8.22 8.40 |
| 15. | 4-chloro-phenyl | $CH_3$ | H | $COOC_2H_5$ | carbontetra-chloride | — | 183–185 n-propanol | 85 | 63.60 63.42 Cl 9.88 Cl 9.78 | 5.34 5.12 | 7.81 8.00 |
| 16. | 2-phenyl-vinyl | $CH_3$ | H | $COOC_2H_5$ | carbontetra-chloride | — | 167–169 n-propanol | 75 | 71.98 71.60 | 6.33 6.32 | 7.99 8.15 |
| 17. | 4-methoxy-phenyl | $CH_3$ | H | $COOC_2H_5$ | carbontetra-chloride | — | 114–116 ethanol | 61 | 67.78 67.58 | 6.26 6.28 | 7.90 8.02 |
| 18. | 2-hydroxy-phenyl | $CH_3$ | H | $COOC_2H_5$ | carbontetra-chloride | — | 200–201 dioxane | 81 | 67.05 66.82 | 5.92 6.01 | 8.23 8.34 |
| 19. | 4-dimethyl-amino-phenyl | $CH_3$ | H | $COOC_2H_5$ | carbontetra-chloride | — | 161–162 ethanol | 81 | 68.64 68.32 | 6.86 6.74 | 11.44 11.59 |
| 20. | 2-(2-nitro-phenyl)-vinyl | $CH_3$ | H | $COOC_2H_5$ | ethanol | HCl | 166–168 propanol | 77 | 63.79 63.60 | 5.35 5.41 | 10.63 10.54 |
| 21. | 2-chloro-phenyl | $CH_3$ | H | $COOC_2H_5$ | ethanol | — | 138–140 ethanol | 50 | 63.60 63.81 Cl 9.88 Cl 10.02 | 5.34 5.29 | 7.81 7.88 |
| 22. | 2-nitro-phenyl | $CH_3$ | H | $COOC_2H_5$ | ethanol | HCl | 158–159 ethanol | 50 | 61.78 61.63 | 5.19 5.15 | 11.38 11.58 |
| 23. | 4-nitro-phenyl | $CH_3$ | H | $COOC_2H_5$ | benzene | p-toluene-sulfonic-acid | 218–220 ethyl-acetate | 46 | 61.78 61.49 | 5.19 5.15 | 11.38 11.35 |
| 24. | 2-ethoxy-phenyl | $CH_3$ | H | $COOC_2H_5$ | benzene | p-toluene-sulfonic acid | 149–151 ethanol | 44 | 68.46 68.34 | 6.57 6.46 | 7.60 7.56 |
| 25. | 3-nitro-phenyl | $CH_3$ | H | $COOC_2H_5$ | benzene | p-toluene-sulfonic-acid | 151–153 ethanol | 46 | 61.78 61.88 | 5.19 5.13 | 11.38 11.26 |
| 26. | 3,4-dichloro-phenyl | $CH_3$ | H | $COOC_2H_5$ | benzene | p-toluene-sulfonic acid | 148–150 ethanol | 51 | 58.03 58.03 | 4.61 4.51 | 7.12 7.08 |
| 27. | 3-cyano-phenyl | $CH_3$ | H | $COOC_2H_5$ | benzene | p-toluene-sulfonic-acid | 148– ethanol | 20 | 68.76 69.08 | 5.48 5.36 | 12.03 12.07 |
| 28. | 3-pyridyl | $CH_3$ | H | $COOC_2H_5$ | benzene | p-toluene-sulfonic acid | 108–110 ethanol | 37 | 66.86 66.65 | 5.30 5.40 | 13.00 12.98 |
| 29. | 4-acetylamino-phenyl | $CH_3$ | H | $COOC_2H_5$ | benzene | p-toluene-sulfonic acid | 212–214 ethanol | 86 | 64.62 64.60 | 6.84 6.80 | 9.83 9.89 |
| 30.*** | carboxy | $CH_3$ | H | $COOC_2H_5$ | ethanol | — | 167–168 ethanol | 73 | 57.53 57.65 | 5.52 5.48 | 9.58 9.70 |
| 31.* | carboxy | $CH_3$ | H | $COOC_2H_5$ | ethanol | — | 168–170 | 72 | 57.53 | 5.52 | 9.58 |

TABLE 3-continued $$\text{structure with } R_{16}\text{—CH, } R_{17}, R_{18}, R_{19}$$

| No. | $R_{16}$ | $R_{17}$ | $R_{18}$ | $R_{19}$ | Solvent | Catalyst | M.p. °C. solvent used for crystallization | Yield % | C% | H% | N% |
|---|---|---|---|---|---|---|---|---|---|---|---|
| | | | | | | | | | Analysis Calculated Found | | |
| 32.** | carboxy | $CH_3$ | H | $COOC_2H_5$ | ethanol | — | 169–171 ethanol | 74 | 57.45 57.53 | 5.70 5.52 | 9.57 9.58 |
| 33. | phenyl | $CH_3$ | H | COOH | xylene | sulfuric acid | 204–205 DMF | 71 | 57.62 68.91 68.68 | 5.46 5.44 5.46 | 9.72 9.45 9.56 |
| 34. | 5-nitro-2-furyl | $CH_3$ | H | COOH | benzene | — | 253–254 DMF | 50 | 54.23 54.55 | 3.96 3.85 | 12.68 12.58 |
| 35. | 2-hydroxy-phenyl | $CH_3$ | H | COOH | benzene | — | 235–236 DMF | 67 | 65.38 65.17 | 5.16 5.10 | 8.97 8.92 |
| 36. | 2-chloro-phenyl | $CH_3$ | H | COOH | xylene | sulfuric acid | 205 DMF | | 61.73 61.64 Cl 10.72 Cl 10.40 | 4.57 4.68 | 8.47 8.56 |
| 37. | 4-chloro-phenyl | $CH_3$ | H | COOH | benzne | — | 222–223 DMF | | 61.73 61.59 Cl 10.72 Cl 10.48 | 4.57 4.51 | 8.47 8.32 |
| 38. | N-methyl-2-pyrryl | $CH_3$ | H | COOH | benzene | — | 210–211 DMF | 33 | 64.20 64.08 | 5.72 5.57 | 14.04 14.10 |
| 39. | 2-nitro-phenyl | $CH_3$ | H | COOH | benzene | — | 199–200 DMF | 73 | 59.82 59.72 | 4.43 4.47 | 12.31 12.21 |
| 40. | 4-hydroxy-phenyl | $CH_3$ | H | COOH | benzene | — | 279–280 DMF | 98 | 65.38 65.42 | 5.16 5.11 | 8.97 8.90 |
| 41. | 2-pyrryl | $CH_3$ | H | COOH | benzene | — | 287–288 DMF | 87 | 63.15 63.47 | 5.30 5.27 | 14.73 14.81 |
| 42. | 3,4-methylene-dioxy-phenyl | $CH_3$ | H | COOH | benzene | — | 247–248 DMF | 85 | 63.53 62.98 | 4.74 4.75 | 8.23 8.23 |
| 43. | carboxy | $CH_3$ | H | COOH | benzene | — | 202–203 ethanol | 95 | 54.60 54.74 | 4.58 4.55 | 10.62 10.56 |
| 44. | 2-(2-nitro-phenyl)-vinyl | $CH_3$ | H | COOH | benzene | — | 234–235 DMF | 62 | 62.13 62.01 | 4.66 4.59 | 11.44 11.41 |
| 45. | 3-hydroxy-4-methoxy-phenyl | $CH_3$ | H | COOH | benzene | — | 256–257 DMF | 79 | 63.14 63.14 | 5.30 5.38 | 8.18 8.27 |
| 46. | 3,4,5-trimethoxy-phenyl | $CH_3$ | H | COOH | benzene | — | 184–185 DMF | 90 | 62.17 62.03 | 5.74 5.53 | 7.25 7.20 |
| 47. | 4-methoxy-phenyl | $CH_3$ | H | COOH | benzene | — | 195–196 DMF | 64 | 66.25 66.42 | 5.56 5.56 | 8.58 8.49 |
| 48. | 2-furyl | $CH_3$ | H | COOH | benzene | — | 225–227 DMF | 90 | 62.93 62.84 | 4.93 4.88 | 9.79 9.77 |
| 49. | 2-phenyl-vinyl | $CH_3$ | H | COOH | benzene | — | 223–224 DMF | 78 | 70.80 70.86 | 5.63 5.50 | 8.69 8.75 |
| 50. | 3,4-dimethoxy-phenyl | $CH_3$ | H | COOH | benzene | — | 222 DMF | | 64.04 64.30 | 5.66 5.61 | 7.86 7.73 |
| 51. | 4-dimethylamino-phenyl | $CH_3$ | H | COOH | benzene | — | 228–229 DMF | 97 | 67.24 67.48 | 6.24 6.18 | 12.38 12.26 |
| 52 | 4-hydroxy-3-methoxy-phenyl | $CH_3$ | H | COOH | benzene | — | 254–255 DMF | 67 | 63.14 62.98 | 5.30 5.32 | 8.18 8.11 |
| 53. | 5-nitro-2-furyl | $CH_3$ | H | $CH_3$ | benzene | acetic acid | 183–184 ethanol | 46 | 59.80 60.07 | 5.02 5.06 | 13.95 14.06 |
| 54. | 5-nitro-2-furyl | $CH_3$ | H | CONHN=<br>=CH—(5-nitro-2-furyl) | dimethyl formamide | — | 288–290 DMF | 53 | 51.28 50.86 | 3.44 3.47 | 17.94 17.76 |
| 55. | 5-nitro-2-furyl | $CH_3$ | H | $CONH_2$ | methanol | — | 278–280 DMF | 68 | 54.54 54.50 | 4.27 4.15 | 16.96 16.91 |
| 56. | 5-nitro-furyl | H | H | $C_6H_5$ | acetone | HCl | 245–246 DMF | 61 | 65.32 65.25 | 4.33 4.02 | 12.03 11.97 |
| 57. | 5-nitro-2-furyl | $CH_3$ | H | H | formamide | — | 196 dioxane | 80 | 58.23 56.15 | 4.57 4.49 | 14.63 14.60 |
| 58. | 5-nitro-2-furyl | H | H | $COOC_2H_5$ | chloroform | — | 240 DMF | 82 | 55.65 55.45 | 4.38 4.28 | 12.17 12.12 |
| 59. | 5-nitro-2-furyl | $CH_3$ | $CH_3$ | H | ethanol | HCl | 235 n-propanol | 63 | 59.80 60.07 | 5.02 5.15 | 13.95 14.01 |
| 60. | 5-nitro-2-furyl | H | $CH_3$ | H | ethanol | HCl | 217 ethanol | 66 | 58.25 58.03 | 4.56 4.50 | 14.63 14.40 |
| 61. | carboxy | $CH_3$ | H | $CONH_2$ | ethanol | — | 242 DMF | 85 | 54.75 54.60 | 4.98 5.09 | 15.96 15.83 |
| 62. | carboxy | H | H | $COOC_2H_5$ | ethanol | — | 170–171 | 81 | 56.11 | 5.07 | 10.07 |

TABLE 3-continued structure with $R_{16}$-CH=, ring with N, N, O, $R_{17}$, $R_{18}$, $R_{19}$ substituents

| No. | $R_{16}$ | $R_{17}$ | $R_{18}$ | $R_{19}$ | Solvent | Catalyst | M.p. °C. solvent used for crystallization | Yield % | Analysis Calculated Found C% | H% | N% |
|---|---|---|---|---|---|---|---|---|---|---|---|
| 63. | carboxy | $CH_3$ | H | $COOCH_3$ | ethanol | — | ethanol 160–162 ethanol | 90 | 56.18 56.11 55.99 | 5.10 5.07 5.01 | 9.85 10.07 9.82 |
| 64. | carboxy | $CH_3$ | H | COOCH(CH_3)(CH_3) | ethanol | — | 205–206 ethanol | 85 | 58.82 58.91 | 5.92 6.02 | 9.16 9.09 |
| 65. | carboxy | $CH_3$ | H | $COO(CH_2)_2CH_3$ | ethanol | — | 167–168 ethanol | 80 | 58.82 58.42 | 5.92 5.87 | 9.16 9.19 |
| 66. | carboxy | $CH_3$ | H | $COO(CH_2)_3CH_3$ | ethanol | — | 140–141 ethanol | — | 59.99 60.02 | 6.29 6.15 | 8.75 8.73 |
| 67. | carboxy | $CH_3$ | H | $CH_2COOC_2H_5$ | benzene | — | 123–124 ethylacetate | — | 59.40 59.56 | 4.99 5.07 | 9.24 9.20 |
| 68. | carboxy | $CH_3$ | H | H | benzene | — | 213–214 ethanol | 60 | 59.99 59.94 | 5.49 5.52 | 12.72 12.53 |
| 69. | carboxy | $CH_3$ | H | $CH_3$ | benzene | — | 239–240 ethanol | 40 | 61.53 61.58 | 6.03 5.81 | 11.96 12.01 |
| 70. | carboxy | $CH_3$ | H | $C_6H_5$ | benzene | — | 210–211 methanol | 54 | 68.44 68.56 | 6.08 6.12 | 9.39 9.38 |
| 71. | carboxy | $CH_3$ | H | CN | ethanol | — | 242–243 DMF-ethanol | 45 | 58.77 59.00 | 4.52 4.47 | 17.13 17.18 |
| 72. | carboxy | $CH_3$ | $CH_3$ | H | ethanol | HCl | 227 | 65 | 61.53 61.84 | 6.02 6.22 | 11.96 11.82 |
| 73. | carboxy | H | $CH_3$ | H | ethanol | HCl | 254 | 45 | 59.99 59.83 | 5.49 5.49 | 12.72 12.61 |

*$[\alpha]_D^{20} = -217°$ (c = 2,methanol)
**$[\alpha]_D^{20} = +216°$ (c = 2,methanol)
***by the preparation of compounds wherein $R^{16}$ is carboxy, as aldehyde component glyoxilic acid or glyoxilic acid monohydrate may be used.

EXAMPLE 74

23.6 g of 3-ethoxycarbonyl-7-methyl-4-oxo-6,7,8,9-tetrahydro-4H-pyrido(1,2a)pyrimidine and 10.0 g of glyoxylic acid monohydrate are reacted and the obtained 3-ethoxycarbonyl-7-methyl-9-(carboxy-(hydroxymethyl)-4-oxo-6,7,8,9-tetrahydro-4H-pyrido(1,2a)-pyrimidine is heated in 150 ml ethanol under stirring for 3 hours. After cooling the crystals are filtered off and recrystalized from ethanol. Thus 3-ethoxycarbonyl-7-methyl-9-(carboxy-methylene)-4-oxo-6,7,8,9-tetrahydro-4H-pyrido-(1,2a)pyrimidine melting at 110° to 112° C. is obtained.

Yield: 51%.

Analysis: Calculated: C 57.53%, H 5.52%, N 9.58%: Found: C 57.32%, H 5.60%, N 9.56%.

EXAMPLE 75

The benzene mother liquor obtained by example 17 is evaporated in vacuo. The residue is dissolved in 10 ml of ethanol whereupon 15 ml of ethanol containing 16% hydrochloric acid are added. The 3,6-dimethyl-9-(5-nitro-2-furfurylidene)-4-oxo-6,7,8,9-tetrahydro-4H-pyrido(1,2a)pyrimidinium-hydrochloride melts at 215°–216° C. after recrystallization from ethanol.

Analysis: Calculated: C 53.34%, H 4.78%, N 12.44%, Cl 10.50%: Found: C 53.22%, H 4.83%, N 12.55%, Cl 10.55%.

EXAMPLE 76

3-ethoxycarbonyl-9-(1'-phenylamino-benzyl)-6-methyl-4-oxo-6,7,8,9-tetrahydro-4H-pyrido(1,2a)pyrimidine obtained by reacting 47.2 g of 3-ethoxycarbonyl-6-methyl-4-oxo-6,7,8,9-tetrahydro-4H-pyrido(1,2a)-pyrimidine and 36.2 g of benzalaniline is stirred in a water bath for 8 hours, whereupon 3-ethoxycarbonyl-9-benzylidene-6-methyl-4-oxo-6,7,8,9-tetrahydro-4H-pyrido(1,2a)pyrimidine is obtained accompanied by the formation of aniline. The reaction mixture is dissolved in 300 ml of benzene and shaken out with 5 percent by weight solution of hydrochloric acid in water. The benzene phase is dried, evaporated and the residue is recrystallized from ethanol twice. Yellow 3-ethoxycarbonyl-9-benzylidene-6-methyl-4-oxo-6,7,8,9-tetrahydro-4H-pyrido(1,2a)pyrimidine melting at 138° to 139° C. is obtained. The product does not give any decrease in the melting point of the product prepared according to Example 5 when admixed therewith.

EXAMPLE 77

55.6 g of 3-ethoxycarbonyl-9-(carboxy-methylene)-4-oxo-6,7,8,9-tetrahydro-4H-pyrido(1,2a)pyrimidine are hydrogenated in 500 ml of ethanol in the presence of 20 g of 9 percent by weight Pd/C catalyst containing metal. When 1 mole of hydrogen has been used up, the catalyst is removed from the reaction mixture by filtration and the solution is evaporated under reduced pressure. The residue is recrystallized from ethanol. 3-ethoxycarbonyl-4-oxo-6,7,8,9-tetrahydro-4H-pyrido(1,2a)pyrimidine-9-acetic acid melting at 156° to 157° C. is obtained.

Yield: 57%

Analysis: Calculated: C 55.71%, H 5.75%, N 10.00%: Found: C 55.51%, H 5.62%, N 10.07%.

According to the method described in Example 77 using the appropriate starting material the following compounds listed in Table 4 are obtained.

TABLE 4

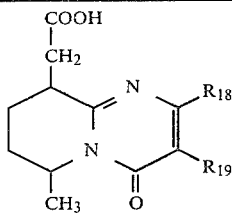

| No. | $R_{18}$ | $R_{19}$ | M.p. °C. solvent used for cryst. | Yield | Analysis Calculated Found C% | H% | N% |
|---|---|---|---|---|---|---|---|
| 78. | H | $COOC_2H_5$ | 153–154 | 68 | 57.14 | 6.17 | 9.52 |
|  |  |  | ethanol |  | 57.02 | 6.22 | 9.54 |
| 79.* | H | $COOC_2H_5$ | 130–132 | 75 | 57.14 | 6.17 | 9.52 |
|  |  |  | ethanol |  | 57.23 | 6.20 | 9.51 |
| 80.** | H | $COOC_2H_5$ | 133–134 | 68 | 57.14 | 6.17 | 9.52 |
|  |  |  | ethanol |  | 57.10 | 6.30 | 9.60 |
| 81. | H | $C_6H_5$ | 162–164 | 89 | 68.44 | 6.08 | 9.39 |
|  |  |  | ethanol |  | 68.06 | 6.00 | 9.28 |
| 82. | H | $COOCH_3$ | 215 | 80 | 55.71 | 5.75 | 9.99 |
|  |  |  |  |  | 55.65 | 5.72 | 10.03 |
| 83. | H | $COOCH(CH_3)_2$ | 148 | 60 | 58.43 | 6.54 | 9.09 |
|  |  |  | ethanol |  | 58.05 | 6.57 | 8.98 |
| 84. | H | $COO(CH_2)_2CH_3$ | 137 | 57 | 58.43 | 6.54 | 9.09 |
|  |  |  | ethanol |  | 58.20 | 6.34 | 8.94 |
| 85. | H | H | 178 | 65 | 59.45 | 6.35 | 12.60 |
|  |  |  | ethanol |  | 59.36 | 6.43 | 12.71 |
| 86. | $CH_3$ | H | 175–176 | 68 | 61.00 | 6.83 | 11.86 |
|  |  |  | ethanol |  | 60.96 | 6.86 | 11.90 |

*$[\alpha]_D^{20} = -164°$ (c = 1, methanol)
**$[\alpha]_D^{20} = +165°$ (c = 1, methanol)

EXAMPLE 87

34.0 g of 3-ethoxycarbonyl-9-(carboxy-methylene)-4-oxo-6,7,8,9-tetrahydro-4H-pyrido(1,2a)pyrimidine are hydrogenated in 600 ml of ethanol in the presence of 20 g of 9 percent by weight Pd/C catalyst containing metal. When 2 moles of hydrogen have been used up, the catalyst is filtered off from the reaction mixture and the mixture is evaporated under reduced pressure. The residue is recrystallized from ethanol. 3-ethoxycarbonyl-4-oxo-1,6,7,8,9,9a-hexahydro-4H-pyrido(1,2a)-pyrimidine-9-acetic acid melting at 205° C. is obtained.

Analysis: Calculated: C 55.31%, H 6.43%, N 9.92%: Found: C 55.25%; H 6.32%, N 10.03%.

EXAMPLE 88

29.4 g of 3-methoxycarbonyl-6-methyl-4-oxo-6,7,8,9-tetrahydro-4H-pyrido(1,2a)pyrimidine-9-acetic acid methylester are dissolved in methanol at 10° C. The aqueous solution of 5 g of sodiumborohydride is added to the solution dropwise. The precipitated crystals are filtered off, and washed with water and then with methanol. 3-methoxycarbonyl-6-methyl-4-oxo-1,6,7,8,9,9a-hexahydro-4H-pyrido(1,2a)pyrimidine-9-acetic acid methylester is obtained. Yield: 89%.

The melting point after recrystallization from dimethylformamide is 225° to 226° C. (decomp.)

Analysis: Calculated: C 56.75%, H 6.80%, N 9.45%: Found: C 56.74%, H 6.89%, N 9.63%.

EXAMPLE 89

According to the method described in Example 88 but starting from 3-ethoxycarbonyl-6-methyl-4-oxo-6,7,8,9-tetrahydro-4H-pyrido(1,2a)pyrimidine-9-acetic acid ethyl ester. 3-ethoxycarbonyl-6-methyl-4-oxo-1,6,7,8,9,9a-hexahydro-4H-pyrido(1,2a)pyrimidine-9-acetic acid ethyl ester is obtained. Melting point after recrystallization from dimethylformamide 206° C. Yield: 56%.

Analysis: Calculated: C 59.25%, H 7.46%, N 8.64%: Found: C 59.03%, H 7.56%, N 8.63%.

EXAMPLE 90

55.6 g of 3-ethoxycarbonyl-9-(carboxy-methylene)-4-oxo-6,7,8,9-tetrahydro-4H-pyrido(1,2a)pyrimidine are suspended in 400 ml of ethanol. The reaction mixture is saturated with hydrogen chloride gas under stirring and external cooling, then allowed to stand at room temperature overnight. Ethanol is distilled off under reduced pressure and the obtained residue is recrystallized from ethanol. 3-ethoxycarbonyl-9-(ethoxycarbonyl-methylene)-4-oxo-6,7,8,9-tetrahydro-4H-pyrido-(1,2a)-pyrimidine melting at 120° to 121° C. is obtained. Yield: 90%.

Analysis: Calculated: C 58.82%, H 5.92%, N 9.15%: Found: C 58.72%, H 5.70%, N 9.29%.

According to the method described in Example 90 using the appropriate starting material the following compounds listed in Table 5 are prepared.

TABLE 5

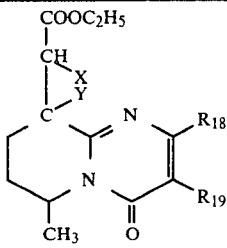

| No. | $R_{18}$ | $R_{19}$ | X | Y | M.p. °C. solvent used for cryst. | Analysis Calculated Found C% | H% | N% | Yield % |
| --- | --- | --- | --- | --- | --- | --- | --- | --- | --- |
| 91. | H | COOC$_2$H$_5$ | valency bond | | 133–135 isopropanol | 59.99 59.48 | 6.29 6.22 | 8.75 9.01 | 82 |
| 92.* | H | COOC$_2$H$_5$ | valency bond | | 121–123 isopropanol | 59.99 59.78 | 6.29 6.32 | 8.75 8.74 | 69 |
| 93.** | H | COOC$_2$H$_5$ | valency bond | | 122–123 isopropanol | 59.99 60.12 | 6.29 6.20 | 8.75 8.79 | 65 |
| 94. | H | H | valency bond | | 120 ethanol | 62.89 62.95 | 6.50 6.51 | 11.28 11.19 | 68 |
| 95. | H | C$_6$H$_5$ | valency bond | | 129–131 isopropanol | 70.35 70.62 | 6.22 6.30 | 8.64 8.76 | 85 |
| 96. | CH$_3$ | H | valency bond | | 124–126 ethanol | 64.11 64.23 | 6.92 6.94 | 10.68 10.80 | 74 |
| 97. | H | COOC$_2$H$_5$ | H | H | oil | 59.63 59.90 | 6.88 6.80 | 8.69 8.61 | 65 |
| 98. | H | H | H | H | 78–79 petrol-ether | 62.89 62.38 | 6.50 6.42 | 11.28 11.12 | 84 |
| 99. | CH$_3$ | H | H | H | 71–73 petrol-ether | 63.62 63.76 | 7.63 7.72 | 10.60 10.61 | 60 |

*$[\alpha]_D^{20} = -215°$ (c = 2, methanol)
**$[\alpha]_D^{20} = +215.5°$ (c = 2, methanol)

EXAMPLE 100

14.7 g of 3-ethoxycarbonyl-6-methyl-4-oxo-6,7,8,9-tetrahydro-4H-pyrido(1,2a)pyrimidine-9-acetic acid are heated in the mixture of 23 g of ethanol and 5 ml of sulphuric acid for 5 hours, whereupon the ethanol is distilled off under reduced pressure and the residue is poured on ice and shaken out with chloroform. The chloroform solution is dried and evaporated under reduced pressure. Ethylacetate is distilled through the residue. 3-ethoxycarbonyl-6-methyl-4-oxo-6,7,8,9-tetrahydro-4H-pyrido-(1,2a)pyrimidine-9-acetic acid ethylester is obtained in the form of non-crystallizing yellow oil. Yield: 50%.

Analysis: Calculated: C 59.62%, H 6.88%, N 8.69%:
Found: C 60.02%, H 6.90%, N 8.65%.

EXAMPLE 101

According to the process described in Example 100 but starting from 3-ethoxycarbonyl-6-methyl-9-(carboxymethylene)-4-oxo-6,7,8,9-tetrahydro-4H-pyrido(1,2a)-pyrimidine 3-ethoxycarbonyl-6-methyl-9-(ethoxycarbonyl-methylene)-4-oxo-6,7,8,9-tetrahydro-4H-pyrido(1,2a)pyrimidine is obtained. The product does not give any decrease in melting point when admixed with one product of Example 91.

EXAMPLE 102

14.7 g of 3-ethoxycarbonyl-6-methyl-4-oxo-6,7,8,9-tetrahydro-4H-pyrido(1,2a)pyrimidine-9-acetic acid are heated in the mixture of 4.6 g of ethanol, 0.25 g of sulphuric acid and 25 ml of chloroform and the water deliberating during the esterification is continuously collected in a water separator.

The reaction mixture is shaken out with 2-fold 30 ml of 5 percent by weight sodium carbonate solution, dried and the chloroform is distilled off under reduced pressure. Thus 3-ethoxycarbonyl-6-methyl-4-oxo-6,7,8,9-tetrahydro-4H-pyrido-(1,2a)pyrimidine-3-acetic acid ethyl ester is obtained in the form of non-crystallizing oil.

Analysis: Calculated: C 59.62%, H 6.88%, N 8.69%:
Found: C 59.70%, H 6.98%, N 8.54%.

EXAMPLE 103

According to the process described in Example 102 but starting from 3-ethoxycarbonyl-6-methyl-9-(carboxymethylene)-4-oxo-6,7,8,9-tetrahydro-4H-pyrido(1,2a)-pyrimidine-3-ethoxycarbonyl-6-methyl-9-(ethoxycarbonyl-methylene)-4-oxo-6,7,8,9-tetrahydro-4H-pyrido(1,2a)pyrimidine melting at 134° to 135° C. is obtained. The product does not give any decrease in the melting point when admixed with the product of the Example 91 and 100, respectively.

EXAMPLE 104

43.84 g of 3-ethoxycarbonyl-6-methyl-9-(carboxymethylene)-4-oxo-6,7,8,9-tetrahydro-4H-pyrido(1,2a)-pyrimidine are suspended in 400 ml of methanol. The mixture is saturated with hydrogen chloride gas under stirring, at 0° to 5° C. and the reaction mixture is allowed to stand in a refrigerator overnight. The reaction mixture is evaporated under reduced pressure and the residue is admixed with 200 ml of water. The precipitated crystals are filtered off, washed with water and recrystallized from n-propanol. 3-methoxy-carbonyl-6-methyl-9-(methoxycarbonyl-methylene)-4-oxo-6,7,8,9-tetrahydro-4H-pyrido-(1,2a)pyrimidine is obtained. Melting point: 135° to 137° C.

Yield: 80%.

Analysis: Calculated: C 57.53%, H 5.52%, N 9.58%: Found: C 57.66%, H 5.34%, N 9.60%.

EXAMPLE 105

50 g of 3-ethoxycarbonyl-6-methyl-4-oxo-6,7,8,9-tetrahydro-4H-pyrido(1,2a)pyrimidine-9-yl-acetic acid are dissolved in methanol and gaseous hydrogen chloride is introduced for 5 hours at −10° C. The reaction mixture is allowed to stand at room temperature over night and evaporated in vacuo. The residue is dissolved in water and the pH of the solution is adjusted to 7 with aqueous sodium hydrogen carbonate solution. After extraction with benzene and drying and evaporation of the extract 3-methoxycarbonyl-6-methyl-4-oxo-6,7,8,9-tetrahydro-4H-pyrido(1,2a)pyrimidine-9-acetic acid methyl ester are obtained.

Mp.: 101°–103° C. after recrystallization from ethyl acetate.

Yield: 67%.

Analysis: Calculated: C 57.14%, H 6.17%, N 9.52%: Found: C 57.57%, H 6.34%, N 9.50%.

EXAMPLE 106

58.8 of 3-methoxycarbonyl-6-methyl-4-oxo-6,7,8,9-tetrahydro-4H-pyrido(1,2a)pyrimidine-9-acetic acid methyl ester are stirred with aqueous sodium hydroxide solution. The reaction mixture is neutralized with hydrochloric acid. The precipitated crystals are filtered off. Thus 3-carboxy-6-methyl-4-oxo-6,7,8,9-tetrahydro-4H-pyrido(1,2a)-pyrimidine-9 acetic acid are obtained. Yield: 75%.

Mp.: 190° C., decomposition, after recrystallization from n-propanol.

Analysis: Calculated: C 54.13%, H 5.30%, N 10.52%: Found: C 54.17%, H 5.32%, N 10.31%.

EXAMPLE 107

0.65% of magnesium is reacted with 20 ml of ethanol in the presence of 0.1 g of iodine as catalyst. To the magnesiumethylate solution thus obtained 14.7 g of 3-ethoxycarbonyl-6-methyl-4-oxo-6,7,8,9-tetrahydro-4H-pyrido(1,2a)pyrimidine-9-acetic acid and 300 ml of ethanol are added. The reaction mixture is heated to boiling, filtered off and the filtrate is evaporated in vacuo. Thus 13.0 g of crude magnesium-3-ethoxycarbonyl-6-methyl-4-oxo-6,7,8,9-tetrahydro-4H-pyrido(1,2a)-pyrimidine-9-acetate are obtained.

M.p: above 360° C. decomposition, after recrystallization from a mixture of ethanol and ethyl acetate.

Analysis: Calculated: C 55.05%, H 5.60%, N 9.17%: Found: C 54.18%, H 5.68%, N 8.93%.

EXAMPLE 108

50 g of 3-(ethoxycarbonyl-methyl)-6-methyl-4-oxo-6,7,8,9-tetrahydro-4H-pyrido(1,2a)pyrimidine are reacted with 28.2 g of 5-nitro-2-furfurol and the obtained 3-(ethoxycarbonyl-methyl)-6-methyl-9-(5-nitro-2-furyl)-hydroxymethyl-4-oxo-6,7,8,9-tetrahydro-4H-pyrido(1,2a)pyrimidine is boiled without separation in the mixture of 600 ml of benzene and 2 ml of 16 percent weight solution of hydrochloric acid in ethanol in a flask equipped with a water separator, and then the reaction mixture is evaporated under reduced pressure. The obtained residue is recrystallized from ethanol containing hydrochloric acid twice. Thus 3-(ethoxycarbonyl-methyl)-6-methyl-9-(5-nitro-2-furfurylidene)-4-oxo-6,7,8,9-tetrahydro-4H-pyrido(1,2a)pyrimidinium hydrochloride is obtained.

Yield: 72%.

Analysis: Calculated: C 52.76%, H 4.92%, N 10.43%, Cl 8.65%: Found: C 52.98%, H 4.86%, N 10.26%, Cl 8.63%.

EXAMPLE 109

750 g of 3-ethoxycarbonyl-6-methyl-4-oxo-4H-pyrido-(1,2a)pyrimidine-9-yl-acetic acid are homogenized with 1050 g of crystalline cellulose and 140 g of amylopectine. Granules are formed with 155 g of Eudragite lacquer solution, whereupon it is dried at 40° C., regranulated and homogenized with a powder mixture of 20 g of talc and 20 g of magnesium stearate. Tablets weighing 200 mg and containing 75 mg of active ingredient are pressed in a known manner.

EXAMPLE 110

1500 g of 3-ethoxycarbonyl-6-methyl-4-oxo-6,7,8,9-tetrahydro-4H-pyrido(1,2a)pyrimidine-9-yl-acetic acid, 1500 g of crystalline cellulose, 250 g of polyvinyl pyrolidone are admixed in powdered form in a homogenisator. The powder mixture is granulated with a propanolic solution of 45 g of Eudragit. The granules are dried at 50° C., regranulated and homogenized with a powder mixture of 65 g of talk and 45 g of magnesium stearate. Thus tablets weighing 345 mg and containing 150 mg of the active ingredient are pressed in a known manner. The dragee core thus obtained can be equipped with a film or sugar layer in a known manner.

EXAMPLE 111

100 g of 3-ethoxycarbonyl-6-methyl-4-oxo-6,7,8,9-tetrahydro-4H-pyrido(1,2a)pyrimidine-9-yl-acetic acid are powdered (120 mesh) and homogenized with 5 g of colloidal silicic acid. The powder mixture is uniformly dispersed in 2895 g of molten Witepsol-H at 42° C. From the mass suppositories weighing 3 g and containing 100 g of active ingredient are prepared in a known manner.

The process of Examples 109–111 may also be carried out by using as active ingredient any compound of the formula I in the place of 3-ethoxycarbonyl-6-methyl-4-oxo-4H-pyrido-(1,2a)pyrimidine-9-yl-acetic acid.

What we claim is:

1. A compound of the formula

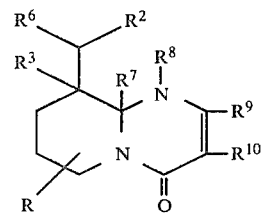

wherein

R is hydrogen or $C_1$ to $C_6$ alkyl in the 6- or 7-position;

$R^2$ is hydrogen or hydroxy;

$R^3$ is hydrogen, or $R^2$ and $R^3$ togehter form a valence bond;

$R^6$ is trihalomethyl, 5-nitro-2-furyl, 2-furyl, 2-pyrryl, N-methyl-2-pyrryl, phenyl, 3,4,5-trimethoxyphenyl, 3-hydroxy-4-methoxyphenyl, 3,4-methylenedioxyphenyl, dimethoxyphenyl, 4-hydroxyphenyl, 4-chlorophenyl, 4-methoxyphenyl, 2-hydroxyphenyl, 4-dimethylaminophenyl, 2-chlorophenyl, 2-nitrophenyl, 4-nitrophenyl, 2-ethoxyphenyl, 3-nitrophenyl, 3,4-dichlorophenyl, 3-cyanophenyl, 4-N-acetylaminophenyl, or pyridyl;

$R^7$ and $R^8$ independently represent hydrogen or together form a valence bond;

$R^9$ is hydrogen or $C_1$ to $C_6$ alkyl;

$R^{10}$ is carboxy or $C_1$ to $C_6$ alkoxycarbonyl; or a pharmaceutically acceptable salt thereof.

2. A compound of the formula:

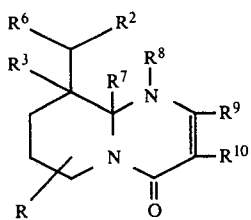

wherein

R is hydrogen or $C_1$ to $C_6$ alkyl in the 6- or 7-position;

$R^2$ is hydrogen or hydroxy;

$R^3$ is hydrogen or $R^2$ and $R^3$ together form a valence bond;

$R^6$ is trihalomethyl, pyridyl, phenyl, phenyl substituted by $C_1$ to $C_6$ alkyl, dialkylamino wherein the alkyl contains 1 to 6 carbon atoms, nitro, $C_1$ to $C_6$ alkoxy, methylenedioxy, cyano or halogen, furyl or pyrryl unsubstituted or substituted by $C_1$ to $C_6$ alkyl, nitro, $C_1$ to $C_6$ alkoxy, halogen, methylenedioxy, or dialkylamino wherein the alkyl contains 1 to 6 carbon atoms;

$R^7$ and $R^8$ independently represent hydrogen or together form a valence bond;

$R^9$ is hydrogen or $C_1$ to $C_6$ alkyl;

$R^{10}$ is carboxy or $C_1$ to $C_6$ alkoxycarbonyl; or a pharmaceutically acceptable salt thereof.

3. 6-methyl-9-(N-methyl-2-pyrryl)-methylene-4-oxo-6,7,8,9-tetrahydro-4H-pyrido(1,2-a)pyrimidine-3-carboxylic acid ethyl ester, as defined in claim 1.

4. 6-methyl-9-(4-chloro-phenyl)-methylene-4-oxo-6,7,8,9-tetrahydro-4H-pyrido(1,2-a)pyrimidine-3-carboxylic acid ethyl ester, as defined in claim 1.

5. 9-(carboxy-methyl)-4-oxo-1,6,7,8,9,9a-hexahydro-4H-pyrido(1,2-a)-pyrimidine-3-carboxylic acid ethyl ester.

6. 9-(methoxycarbonyl-methylene)-6-methyl-4-oxo-6,7,8,9-tetrahydro-4H-pyrido(1,2-a)pyrimidine-3-carboxylic acid methyl ester.

7. An antiatherosclerotic method of treatment which comprises the step of administering to an animal subject in an effective dosage for a period sufficient to ameliorate the condition a compound of the formula:

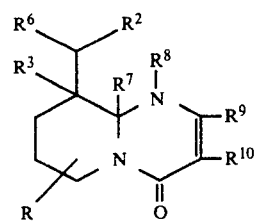

wherein

R is hydrogen or $C_1$ to $C_6$ alkyl in the 6- or 7-position;

$R^2$ is hydrogen or hydroxy;

$R^3$ is hydrogen, or $R^2$ and $R^3$ together form a valence bond;

$R^6$ is carboxy, $C_1$ to $C_6$ alkoxycarbonyl; 5-nitro-2-furyl, 2-furyl, 2-pyrryl, N-methyl-2-pyrryl, phenyl, 3,4,5-trimethoxyphenyl, 3-hydroxy-4-methoxyphenyl, 3,4-methylenedioxyphenyl, dimethoxyphenyl, 4-hydroxyphenyl, 4-chlorophenyl, 4-methoxyphenyl, 2-hydroxyphenyl, 4-dimethylaminophenyl, 2-chlorophenyl, 2-nitrophenyl, 4-nitrophenyl, 2-ethoxyphenyl, 3-nitrophenyl, 3,4-dichlorophenyl, 3-cyanophenyl, 4-N-acetylaminophenyl, or pyridyl;

$R^7$ and $R^8$ independently represent hydrogen or together form a valence bond;

$R^9$ is hydrogen or $C_1$ to $C_6$ alkyl;

$R^{10}$ is carboxy or $C_1$ to $C_6$ alkoxycarbonyl; or a pharmaceutically acceptable salt thereof in combination with a pharmaceutically acceptable inert carrier.

8. An antiatherosclerotic method of treatment which comprises the step of administering to an animal subject in an effective dosage for a period sufficient to ameliorate the condition a compound of the formula:

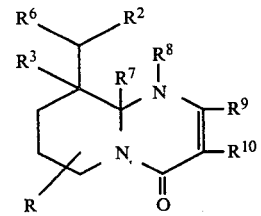

wherein

R is hydrogen or $C_1$ to $C_6$ alkyl in the 6- or 7-position;

$R^2$ is hydrogen or hydroxy;

$R^3$ is hydrogen or $R^2$ and $R^3$ together form a valence bond;

$R^6$ is carboxy, $C_1$ to $C_6$ alkoxycarbonyl trihalomethyl, pyridyl, phenyl, phenyl substituted by $C_1$ to $C_6$ alkyl, dialkylamino wherein the alkyl contains 1 to 6 carbon atoms, nitro, $C_1$ to $C_6$ alkoxy, methylenedioxy, cyano or halogen or furyl or pyrryl unsubstituted or substituted by $C_1$ to $C_6$ alkyl, nitro, $C_1$ to $C_6$ alkoxy, halogen, methylenedioxy, or dialkylamino wherein the alkyl contains 1 to 6 carbon atoms;

$R^7$ and $R^8$ independently represent hydrogen or together form a valence bond;

$R^9$ is hydrogen or $C_1$ to $C_6$ alkyl;

$R^{10}$ is carboxy or $C_1$ to $C_6$ alkoxycarbonyl;

or a pharmaceutically acceptable salt thereof in combination with a pharmaceutically acceptable inert carrier.

9. A compound of the formula:

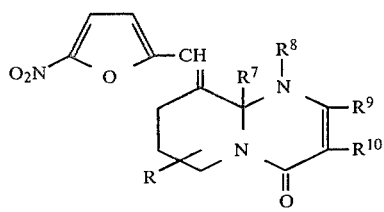

wherein
R is hydrogen, or C$_1$ to C$_6$ alkyl in the 6- or 7-position;
R$^7$ and R$^8$ independently represent hydrogen or together form a valence bond;
R$^9$ is hydrogen or C$_1$ to C$_6$ alkyl;
R$^{10}$ is carboxy, C$_1$ to C$_6$ alkoxycarbonyl,

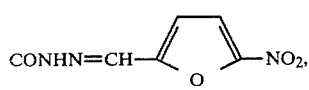

carbamoyl, phenyl, or methyl; or a pharmaceutically acceptable salt thereof.

10. An antiatherosclerotic method of treatment which comprises the step of administering to an animal subject in an effective dosage for a period sufficient to ameliorate the condition a compound of the formula:

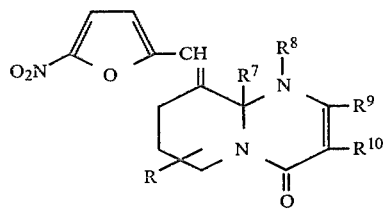

wherein
R is hydrogen or C$_1$ to C$_6$ alkyl in the 6- or 7-position;
R$^7$ and R$^8$ independently represent hydrogen or together form a valence bond;
R$^9$ is hydrogen or C$_1$ to C$_6$ alkyl;
R$^{10}$ is carboxy, C$_1$ to C$_6$ alkoxycarbonyl,

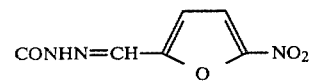

carbamoyl, phenyl, or methyl;
or a pharmaceutically acceptable salt thereof in combination with a pharmaceutically acceptable inert carrier.

11. A compound of the formula:

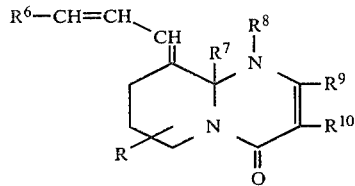

wherein

R is hydrogen or C$_1$ to C$_6$ alkyl in the 6- or 7-position;
R$^6$ is phenyl or nitrophenyl;
R$^7$ and R$^8$ independently represent hydrogen or together form a valence bond;
R$^9$ is hydrogen or C$_1$ to C$_6$ alkyl;
R$^{10}$ is carboxy or C$_1$ to C$_6$ alkoxycarbonyl; or a pharmaceutically acceptable salt thereof.

12. An antiatherosclerotic method of treatment which comprises the step of administering to an animal subject in an effective dosage for a period sufficient to ameliorate the condition a compound of the formula:

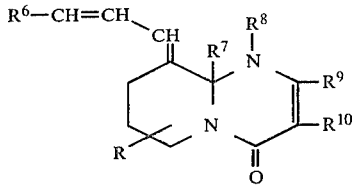

wherein
R is hydrogen or C$_1$ to C$_6$ alkyl in the 6- or 7-position;
R$^6$ is phenyl or nitrophenyl;
R$^7$ and R$^8$ independently represent hydrogen or together form a valence bond;
R$^9$ is hydrogen or C$_1$ to C$_6$ alkyl;
R$^{10}$ is carboxy or C$_1$ to C$_6$ alkoxycarbonyl; or a pharmaceutically acceptable salt thereof.

13. A compound of the formula:

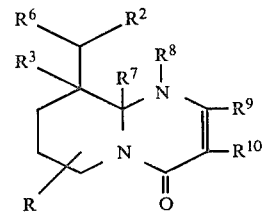

wherein
R is hydrogen or C$_1$ to C$_6$ alkyl in the 6- or 7-position;
R$^2$ and R$^3$ are each hydrogen or together form a valence bond;
R$^6$ is carboxy or C$_1$ to C$_6$ alkoxycarbonyl;
R$^7$ and R$^8$ are each hydrogen or together form a valence bond;
R$^9$ is hydrogen or C$_1$ to C$_6$ alkyl;
R$^{10}$ is carbamoyl, phenyl, cyano, or carboethoxymethyl, or a pharmaceutically acceptable salt thereof.

14. An antiatherosclerotic method of treatment which comprises the step of administering to an animal subject in an effective dosage for a period sufficient to ameliorate the condition a compound of the formula:

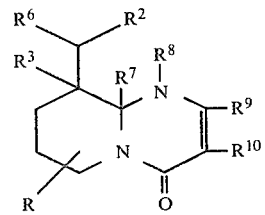

wherein
R is hydrogen or C$_1$ to C$_6$ alkyl in the 6- or 7-position;

$R^2$ and $R^3$ are each hydrogen or together form a valence bond;

$R^6$ is carboxy or $C_1$ to $C_6$ alkoxycarbonyl;

$R^7$ and $R^8$ are each hydrogen or together form a valence bond;

$R^9$ is hydrogen or $C_1$ to $C_6$ alkyl;

$R^{10}$ is carbamoyl, phenyl, cyano or carboethoxymethyl; or a pharmaceutically acceptable salt thereof.

15. 3-ethoxycarbonyl-9-(1-hydroxyl-2,2,2-trichloroethyl)-6-methyl-4-oxo-6,7,8,9-tetrahydro-4H-pyrido(1,2-a)pyrimidine or a pharmaceutically acceptable salt thereof.

16. An antiatherosclerotic method of treatment which comprises the step of administering to an animal subject in an effective dosage for a period sufficient to ameliorate the condition the compound defined in claim 15 or a pharmaceutically acceptable salt thereof.

17. 3-ethoxycarbonyl-9,9-di-(hydroxymethyl)-6-methyl-4-oxo-6,7,8,9-tetrahydro-4H-pyrido(1,2-a)pyrimidine or a pharmaceutically acceptable salt thereof.

18. An antiatherosclerotic method of treatment which comprises the step of administering to an animal subject in an effective dosage for a period sufficient to ameliorate the condition the compound defined in claim 17 or a pharmaceutically acceptable salt thereof.

* * * * *